United States Patent [19]

Mondron

[11] 3,980,706
[45] Sept. 14, 1976

[54] SYNTHESIS OF 2,7-BISDIMETHYLAMINO-10-P-DIMETHYLAMINOPHENYL-9,10-DIHYDRO-9,9-DIMETHYLANTHRACENE

[75] Inventor: Peter J. Mondron, Cleveland, Ohio

[73] Assignee: Horizons Incorporated a division of Horizons Research Incorporated, Cleveland, Ohio

[22] Filed: Nov. 6, 1975

[21] Appl. No.: 629,236

[52] U.S. Cl. .............................. 260/576; 260/618 B
[51] Int. Cl.² ......................................... C07C 85/24
[58] Field of Search ...................... 260/576, 618 B

[56] References Cited
UNITED STATES PATENTS

| | | | |
|---|---|---|---|
| 3,342,595 | 9/1967 | Sprague et al. | 96/90 R |
| 3,660,096 | 5/1972 | Wainer et al. | 96/90 R |

Primary Examiner—Allen B. Curtis
Attorney, Agent, or Firm—Lawrence I. Field

[57] ABSTRACT

The preparation of leucodihydroanthracenes represented by the general formula

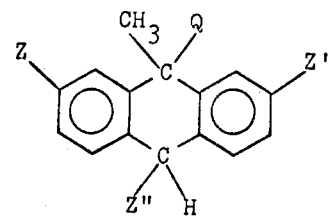

wherein each of Z and Z' is selected from the group consisting of H and dialkylamino, and at least one Z is dialkylamino and each Q is selected from the group consisting of H and alkyl ($C_1$–$C_4$) and Z'' is selected from the group consisting of aryl, alkyl and H, the preferred Z'' being

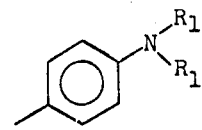

3 Claims, No Drawings

METHYLAMINO DERIVATIVE OF 2-ETHYLINDANDIONE-1,3 AND THE HYDROCHLORIDE THEREOF

CROSS-RELATED APPLICATION

This Application is a continuation of co-pending application Ser. No. 697,278, filed Dec. 27, 1967 and now abandoned.

This invention relates to new chemical compounds, more particularly to amino derivatives of 2-ethylindandion-1,3 of the formula

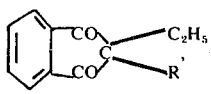

wherein R is a radical selected from the group consisting of

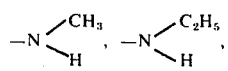

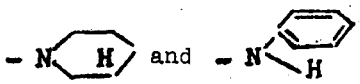

This invention also relates to the hydrochlorides of the above compounds of the same general formula, when R is selected from the group consisting of

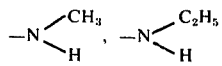

and

The hydrochlorides of the above indicated compounds can be used in medical practice as anticonvulsants, particularly, for the control of epilepsy, as well as intermediates in organic syntheses.

An object of this invention is to provide a process for the preparation of the amino derivatives of 2-ethylindandione-1,3 which consists in treating a methanol solution of propylidenphthalide with a solution of sodium methylate in methanol and the subsequent treatment of the obtained sodium salt of 2-ethylindandione with bromine, followed by amination.

Another object of this invention is to provide a process for the preparation of an amino derivative of 2-ethylindandione-1,3 hydrochloride which consists in dissolving an amino derivative of 2-ethylindandione-1,3 in benzene or diethyl ether or in a mixture thereof and treating them with gaseous hydrogen chloride.

The process of obtaining amino derivatives of 2-ethylindandione-1,3 is carried out as follows.

To a methanol solution of n-propylidenphthalide is added a solution of sodium methylate in methanol and heated in a water bath. A methanol solution of the sodium salt of 2-ethylindandione (of red color) is obtained and treated with bromine, preferably at a temperature under 30°C, until the solution is completely decolorized. The compound 2-bromo-2-ethylindandione-1,3 thus obtained is precipitated with water and extracted with benzene. The benzene solution is separated from the water layer, dried with calcium chloride, treated with a corresponding amine, preferably at a bromine to amine molar ratio of 1:2, at a temperature not over 5°–10°C. The reaction mixture is kept for 1 day at room temperature. Then the precipitated hydrobromide of the initial amine is filtered off and the filtrate is saturated with gaseous hydrochloride. A crude amino derivative of 2-ethylindandione-1,3 hydrochloride is precipitated which is then dissolved in water. The solution thus obtained is treated with an aqueous solution of ammonia in order to extract the amino derivative of 2-ethylindandione-1,3 which is then crystallized from a mixture of ethanol and water. The yield of the amino derivative of 2-ethylindandione-1,3 by the present method reaches approximately 10% of the initial n-propylidenphthalide.

To obtain the hydrochloride, the amino derivative of 2-ethylindandione-1,3 is dissolved in benzene, diethyl ether or in a mixture thereof and treated with gaseous hydrogen chloride; the precipitated hydrochloride of the amino derivative of 2-ethylindandione-1,3 is filtered off, crystallized from absolute ethanol with the addition of diethyl ether and, if necessary, recrystallized.

Synthesized by the above method, the hydrochlorides of the amino derivatives of 2-ethylindandione-1,3 in which R is

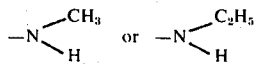

represent new anticonvulsant drugs which in comparison with other widely known anticonvulsant preparations, such as 2-ethyl-2-phenylbarbituric acid, show a much stronger anticonvulsive activity and possess, at the same time, a low acute and chromic toxicity.

One of the advantages of the amino derivatives of 2-ethylindandione-1,3-hydrochlorides is their ready solubility in water without being hydrolyzed. This makes them suitable for parenteral injections. Thus, for instance, in Status Epilepticus a 5–10% sterile aqueous solution of 2-methylamine-2-ethylindandione-1,3 hydrochloride is administered intravenously or intramuscularly or as a medical enoma. The dosage of the injections, depending on the concentration, averages 10–2.5 ml.

For oral application the preparation is issued in tablet form, each tablet containing 250–500 mg of the drug.

In addition, 2-methyl-amino-2-ethylindandione-1,3 hydrochloride is characterized by a high anticonvulsant index, this feature being an essential advantage as compared with the conventional anticonvulsants.

The above indicated salts can be used simultaneously with other available anticonvulsants, for instance, with 4,6-dioxide-5-ethyl-5-phenyltetrahydropyrimidine, or both substances can be used alternatively. By combined administration of these compounds the duration of their protective action is considerably lengthened.

For a better understanding of the present invention, the following examples of producing amino derivatives of 2-ethylindandione-1,3 and their hydrochlorides are presented by way of illustration.

1. A method for synthesizing a 2,7-bis-alkylamine-9,10-dihydro-9,9-dialkylanthracene represented by the general formula:

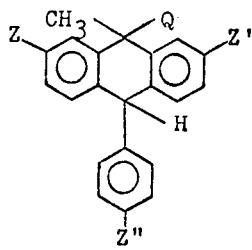

which comprises reacting:

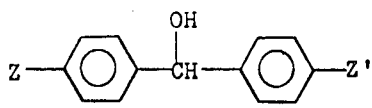

wherein Z and Z' are each selected from the group consisting of H and dialkylamino and at least one of Z and Z' is a dialkylamino group; with

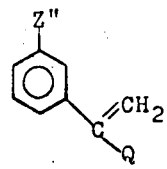

wherein Z'' is selected from the group consisting of H and dialkylamino; Q represents an alkyl group, and thereafter pouring the reacted mixture into concentrated sulfuric acid, maintained at the temperature of melting ice;
then neutralizing the resulting product with a mixture of alkali and cracked ice; and
recovering the resulting anthracene.

2. The method of claim 1 including in addition purifying the resulting anthracene.

3. The process of claim 1 wherein each of Z, Z' and Z'' is dimethylamino.

* * * * * solution of 2-bromo-2-ethylindandione-1,3 is obtained, which is treated with a solution of 68.8 g of piperidino in 200 ml of benzene. The yield is ~ 12 g of 2-piperidino-2-ethylindandione-1,3 (9.2% of the theory calculated on the basis of propyldenphthalide); m.p. 125°C (from ethanol); color of the substance — yellow.

Found,%: N, 5.20. Calculated for $C_{16}H_{19}O_2N$,%: N, 5.44.

I.r. absorption maxima of 2-piperidine-2-ethylindandione-1,3 (crystalline suspension of the compound in paraffine oil);

$\nu_{C=O} = 1697$ and $1729$ cm$^{-1}$; $\nu_{C=C\ arom.} = 1582$ cm$^{-1}$.

Production of 2-piperidine-2-ethylindandione-1,3 hydrochloride

The process is carried out as described in Example 1, but using as solvent 200 ml of diethyl ether or a mixture of 80 ml of benzene and 80 ml of diethyl ether.

The salt represents a crystalline substance of white color, decomp. at 191°–195°C (after two crystallizations from absolute ethanol with diethyl ether added).

Found,%: N, 4.56; Cl, 11.90. Calculated for $C_{16}H_{20}O_2NCl$,%: N, 4.77; Cl, 12.07.

I.r. absorption maxima of 2-piperidine-2-ethylidandione-1,3 hydrochloride (crystalline suspension of the compound in paraffine oil):

$\nu_{C=O} = 1699$ and $1735$ cm$^{-1}$; $\nu_{C=C\ arom.} = 1583$ cm$^{-1}$.

EXAMPLE 4

Production of 2-aniline-2-ethylindandione-1,3

2-bromo-2-ethylindandione-1,3 obtained from 88 g of n-propylidanphthalide are dissolved in 200 ml of ethanol and a solution of 75 g of freshly distilled aniline in 200 ml ethanol is added. The mixture is kept for 1 day and then the solvent and the remaining aniline are vacuum distilled and heated simultaneously in a water bath; the solid residue is washed in water and crystallized from ethanol. The yield is ~30 g (22.3% of theory calculated on the basis of propylidenphthalide) of 2-aniline-2-ethylindandione-1,3 of yellow color; m.p. 150°C.

Found, %: N, 5.31. Calculated for $C_{17}H_{17}O_2N$, %: N, 5.23.

I.r. absorption maxima of 2-aniline-2-ethylindandione-1,3 (crystalline suspension of the compound in paraffine oil):

$\nu_{C=O} = 1708$ and $1743$ cm$^{-1}$; $\nu_{C=C\ arom.} = 1599$ cm$^{-1}$.

2-aniline-2-ethylindandione-1,3 hydrochloride is readily hydrolyzed in water and has therefore no practical application.

Though the present invention has been described in accordance with a preferred embodiment, various changes and modifications may be made in carrying out the invention without departing from the spirit and scope thereof as will be understood by those skilled in the art.

These changes and modifications are to be considered as falling within the spirit and scope of the invention and defined in the appended claims.

Hereinbelow are given assay data concerning the asticonvulsive action of the present compounds (hereinafter referred to as "Metindione").

Anticonvulsive action of Metindione..

Anticonvulsive effect of Metindione in electroshock was studied on white rats and white mice on a comparison basis with the well known drug phenobarbital. Both preparations were administered by intraperitoneal injections. The results are summarized in Tabl. 1 (confidence limits are indicated in parentheses; $P = 0.05$).

Table 1

| Name of Compounds | $ED_{50}$ mg/kg | $ED_{50}$ mg/kg | Protective Index (in ratio of $LD_{50}/ED_{50}$) |
|---|---|---|---|
| Metindione | 3.6(2.8+4.6) | 415(370+465) | 115 (89+149) |
| Phenobarbital | 13.5(9.6+18.9) | 110(100+116) | 8.4(5.6+12.6) |

According to these data the anticonvulsive effect of Metindione, in seizures induced by an electroshock, is almost 4 times stronger than that of phenobarbital and the protective index of Metindione is 14 times higher than that of phenobarbital.

Thirty-day electroshock tests on white mice have shown no necessity to increase the initial dose of Metindione whereas an habit forming reaction to phenobarbital developed almost fully during the same period.

Since Metindione and phenobarbital belong to two different groups of chemical compounds, potentiation of anticonvulsive activity of Metindione by phenobarbital has been studied. It was substantiated in these studies that phenobarbital, in doses small enough not to avert seizures, can prolong almost 8 times the anticonvulsive effect of Metindione.

Influence of Metindione on the rate of development of conditioned reflexes

The influence of Metindione and Phenobarbital on learning has been studied on white mice.

Medium time ($ET_{50}$) required for learning is given in Table 2. (confidence limits are put in parentheses; $P=0.05$).

Table 2

| Name of Compound | Dosage in relation to $ED_{50}$ of anticonv. action | $ET_{50}$ (in day) |
|---|---|---|
| Metindione | ½ | 2.4(2.1+2.6) |
| " | 1 | 2.5(2.1+2.8) |
| " | 2 | 2.0(1.7+2.3) |
| " | 4 | 2.8(2.4+3.4) |
| Phenobarbital | ¼ | 5.6(4.5+6.9) |
| " | ½ | 8.0(6.9+9.3) |
| " | 1 | 9.0(6.9+11.7) |
| Control (saline sol.) | — | 2.9(2.2)+3.8) |

As it can be seen from Table 2, Metindione in indicated doses did not influence the rate of developing conditioned reflexes. Phenobarbital, to the contrary, caused a considerable slowness in this respect even at a dose representing only ¼ of $ED_{50}$ of the anticonvulsive action.

As it is shown in Table 1, Metindione has a low acute and a low chronic toxicity. During an extended every day administration in doses 15 times higher than the therapeutical average, Metindione had no toxic effect and compares favorably in this respect with Phenobarbital. Metindione does not cause any morphological internal organic changes and has no adverse influence on normal development and growth of young animals.

Though the present invention has been described in accordance with a preferred embodiment various changes and modifications may be made in carrying out the invention without departing from the spirit and scope thereof as will be understood by those skilled in the art.
These changes and modifications are to be considered as falling within the spirit and scope of the invention as defined in the appended claims.
What we claim is:
1. The compound
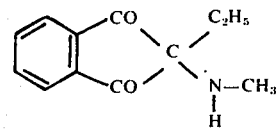
2. The hydrochloride of the compound of claim 1.
* * * * *